(12) United States Patent
Harju et al.

(10) Patent No.: US 7,199,879 B2
(45) Date of Patent: Apr. 3, 2007

(54) VERSATILE INSTRUMENTATION FOR OPTICAL MEASUREMENT OF SAMPLES

(75) Inventors: Raimo Harju, Turku (FI); Janne Salonen, Mynamaki (FI); Hannu Turunen, Raisio (FI)

(73) Assignee: Wallac Oy, Turku (FI)

( * ) Notice: Subject to any disclaimer, the term of this patent is extended or adjusted under 35 U.S.C. 154(b) by 463 days.

(21) Appl. No.: 10/784,997

(22) Filed: Feb. 25, 2004

(65) Prior Publication Data

US 2005/0062969 A1  Mar. 24, 2005

(30) Foreign Application Priority Data

Sep. 19, 2003  (FI) ................................. 20031357

(51) Int. Cl.
*G01N 21/25* (2006.01)
(52) U.S. Cl. .................... 356/417; 356/317; 250/458.1
(58) Field of Classification Search ................ 356/317, 356/318, 417, 73, 244, 246; 422/82.05, 82.06, 422/82.07, 82.08; 250/458.1
See application file for complete search history.

(56) References Cited

U.S. PATENT DOCUMENTS

| 6,097,025 | A | 8/2000 | Modlin et al. |
| 6,329,661 | B1 | 12/2001 | Perov et al. |
| 6,538,735 | B1 | 3/2003 | Duebendorfer et al. |
| 6,825,921 | B1* | 11/2004 | Modlin et al. ................. 356/73 |
| 6,891,618 | B2* | 5/2005 | Harju et al. ................. 356/417 |
| 7,023,553 | B2* | 4/2006 | Harju et al. ................. 356/417 |

FOREIGN PATENT DOCUMENTS

| EP | 1 291 644 A1 | 3/2003 |
| EP | 1 316 794 A1 | 6/2003 |
| WO | WO 03/027741 A2 | 4/2003 |

* cited by examiner

*Primary Examiner*—Layla G. Lauchman
(74) *Attorney, Agent, or Firm*—Young & Thompson

(57) ABSTRACT

The present invention relates generally to the field of biochemical laboratory instrumentation for different applications of measuring properties of samples on e.g. microtitration plates and corresponding sample supports. The object of the invention is achieved by providing an optical measurement instrument for photoluminescence, chemiluminescence and/or AlphaScreen measurements wherein different optical modules are used for alternative measurements. The excitation pulses for the alternative measurements are guided via two different routes to optical modules, the routes reaching the module in different angles. This way it is possible to use alternative radiation sources without optical switches and without changing the optical system. The object of the invention is further achieved by providing an additional lens in the optical module when a thermo plate is used. This way it is possible to achieve a correct optical focus in different measurement modes not depending on the use of the thermo plate.

9 Claims, 4 Drawing Sheets

VERSATILE INSTRUMENTATION FOR OPTICAL MEASUREMENT OF SAMPLES

BACKGROUND OF THE INVENTION

The present invention relates generally to the field of biochemical laboratory instrumentation for different applications of measuring properties of samples on e.g. microtitration plates and corresponding sample supports. More particularly the invention relates to the improved, instrumental features of equipment used as e.g. fluorometers, photometers and luminometers.

The routine work and also the research work in analytical biochemical laboratories and in clinical laboratories are often based on different tags or labels coupled on macromolecules under inspection. The typical labels used are different radioactive isotopes, enzymes, different fluorescent molecules and e.g. fluorescent chelates of rare earth metals.

The detection of enzyme labels can be performed by utilizing its natural biochemical function, i.e. to alter the physical properties of molecules. In enzyme immunoassays colourless substances are catalysed by enzyme to colourful substances or non-fluorescent substances to fluorescent substances.

The colourful substances are measured with absorption, i.e. photometric measurement. In the photometric measurement the intensity of filtered and stabilized beam is first measured without any sample and then the sample inside one plate is measured. The absorbance i.e. the absorption values are then calculated.

The fluorescent measurement is generally used for measuring quantities of fluorescent label substance in a sample. The most photoluminescence labels are based on molecular photoluminescence process. In this process optical radiation is absorbed by the ground state of a molecule. Due to the absorption of energy the quantum molecule rises into higher excited state. After the fast vibrational relaxation the molecule returns back to its ground state and the excess energy is released as an optical quantum. Due to losses in this process the average absorbed energies are higher than the average emitted energies.

A further measurement method is chemiluminescence measurement where emission of a substance is measured from a sample without excitation by illumination. Thus a photoluminometer can also be used as a chemiluminometer.

Further, there is a analysing method called Amplified Luminescent Proximity Homogeneous Assay or AlphaScreen™. The function of the AlphaScreen method is based on the use of small beads that attach to the molecules under study. There are two types of beads that are coated with a material acting either as a donor or acceptor of singlet-state oxygen. The measurement starts, when the liquid sample is illuminated by light with wavelength of 680 nm. After this the material in the donor bead converts ambient oxygen into singlet-state oxygen. The single-state molecules have a short lifetime and they can reach only about a 200 nm distance by diffusion in the liquid. If the chemical reaction in question has taken place, both the donor and acceptor beads are bound to the same molecule and so they are close to each other. In this case the singlet-state oxygen may reach the acceptor bead where a series of reactions is started. As the last phase of the reaction the coating material in the acceptor beads emits photons in the 500–700 nm range. If the chemical reaction has not taken place the singlet-state oxygen cannot reach the acceptor bead and the emission light is not detected. By measuring the intensity of light it is possible to conclude the efficiency of the chemical reaction.

The typical instruments in analytical chemical research laboratories are the different spectroscopic instruments. Many of them are utilizing optical region of electromagnetic spectrum. The two common types of instruments are the spectrophotometers and the spectrofluorometers. These instruments comprise usually one or two wavelength dispersion devices, like monochromators. The dispersion devices make them capable to perform photometric, photoluminescence and chemiluminescense measurements throughout the optical spectrum.

U.S. Pat. No. 6,538,735 describes a prior art device for detecting emission from samples. The principle of the device is illustrated in FIG. 1. The sample is illuminated by high intensity light produced by a light source 12 such as a laser diode. The light transmitted via a fiber bundle 24 excites the sample, which converts the excitation light into emission light upon biomolecular binding occurrence. The emitted light is transmitted via a fiber bundle 20 to a detector, such as a photomultiplier tube, which detects and measures the amount of light after excitation ceases. The fiber bundles that transmit light at the excitation and emission wavelength bands are combined such that the common end of the bundle directly above the well includes both fiber types. The fibers may be combined e.g. coaxially. The system can also include a band-pass filter 36 on the emission side, which eliminates extraneous light, including light corresponding to the excitation wavelength band. The system can be used in assays based on Amplified Luminescent Proximity Homogeneous Assay technique. The amount of light produced by the sample is proportional to the concentration of an analyte in the sample and the excitation wavelength is between 670 to 690 nm. The light can be efficiently generated by employing a high-intensity laser as the excitation source, emitting in the preferred wavelength region. The light emitted from the sample has a wavelength band between about 520 nm and 620 nm. This range is at a shorter wavelength than that of the excitation wavelength band. The device may include a shutter that prevents light from entering the detector while the laser diode is active, and a filter may prevent light outside the emitted wavelength band from entering the detector.

The emitted signal of the AlphaScreen measurement is weak, and the measurement is sensitive to changes in the environment. Therefore there are certain problems related to the prior art arrangements. The described prior art arrangement uses a coaxial optical cable for transmission and detection. When the cross-section of the cable is used for separate optical wires for excitation and detection the usable cross section area is very limited. Therefore both the excitation light pulse and the emission light are much attenuated. The attenuation of the excitation and emission radiation naturally degrades the efficiency and accuracy of the measurements. The attenuation also causes that the instrument needs more calibration.

Another disadvantage of the prior art solutions is that performing different types of measurements require providing separate optics for the photoluminescence measurement and the AlphaScreen measurement. Therefore it takes time to change the measurement type in use, and it is also difficult to upgrade an existing instrument including only a Fluorescence measuring unit with an additional unit for AlphaScreen measurement.

One solution could be providing optical switches for switching the optical route between two light sources. However, optical switches and the related optics also tend to attenuate the radiation and therefore decrease the efficiency of the measurements. Good quality optical switches also tend to increase the manufacturing costs of the instrument significantly.

A further problem relates to maintaining a stable temperature of the samples during the measurement of the whole assay, which is necessary in the AlphaScreen measurement. The temperature could be kept constant by covering the assay tightly with a thermo plate, which has a regulated temperature. However, using a tightly sealed thermo plate just in one type of measurement would mean that different distances should be used between the measurement head and the assay depending on the measurement type. And further, this would bring the problem how to achieve the correct optical focus for the different distances.

SUMMARY OF THE INVENTION

The object of the present invention is to provide an optical instrument for laboratory measurements, wherein the described disadvantages of the prior art are avoided or reduced. The object of the invention is therefore to achieve a measurement instrument with improved versatility, accuracy, reliability, comparability and/or efficiency for performing measurements from samples.

The object of the invention is achieved by providing an optical measurement instrument for photoluminescence, chemiluminescence and/or AplhaScreen measurements wherein different optical modules are used for alternative measurements. The excitation pulses for the alternative measurements are guided via two different routes to optical modules, said routes reaching the modules in different angles. This way it is possible to use separate optical guides for alternative radiation sources without optical switches and without changing the whole optical system. It is also easy to upgrade an instrument with a new type of measurement facility, such as AlphaScreen.

The object of the invention is further achieved by providing an additional lens in the optical module when a thermo plate is used. This way it is possible to achieve a correct optical focus in different measurement modes when the thermo plate is used or not.

An optical measurement instrument according to the invention for measuring samples, comprising a first illumination source for excitation of a sample in a first measurement mode a detector for measuring emission from a sample, a selectable first optical module for guiding the excitation beam to the sample, is characterized in that it comprises a second illumination source for excitation of a sample in a second measurement mode and a selectable second optical module for guiding the excitation beam to the sample, wherein the excitation light beams from the first and second illumination sources are directed to the first and second optical modules in different angles.

According to another aspect of the invention n optical measurement instrument for measuring samples, comprising a first illumination source for excitation of a sample in a first measurement mode a detector for measuring emission from a sample, a selectable first optical module for guiding the excitation beam to the sample, is characterized in that it comprises a second illumination source for excitation of a sample in a second measurement mode and a selectable second optical module for guiding the excitation beam to the sample, wherein the second optical module and/or the first optical module comprises means for adjusting the focus for a shorter distance between the second optical module and the sample than between the first optical module and the sample.

BRIEF DESCRIPTION OF THE DRAWINGS

The described and other advantages of the invention will become apparent from the following detailed description and by referring to the drawings where.

BRIEF DESCRIPTION OF THE DRAWINGS

Figure 1:
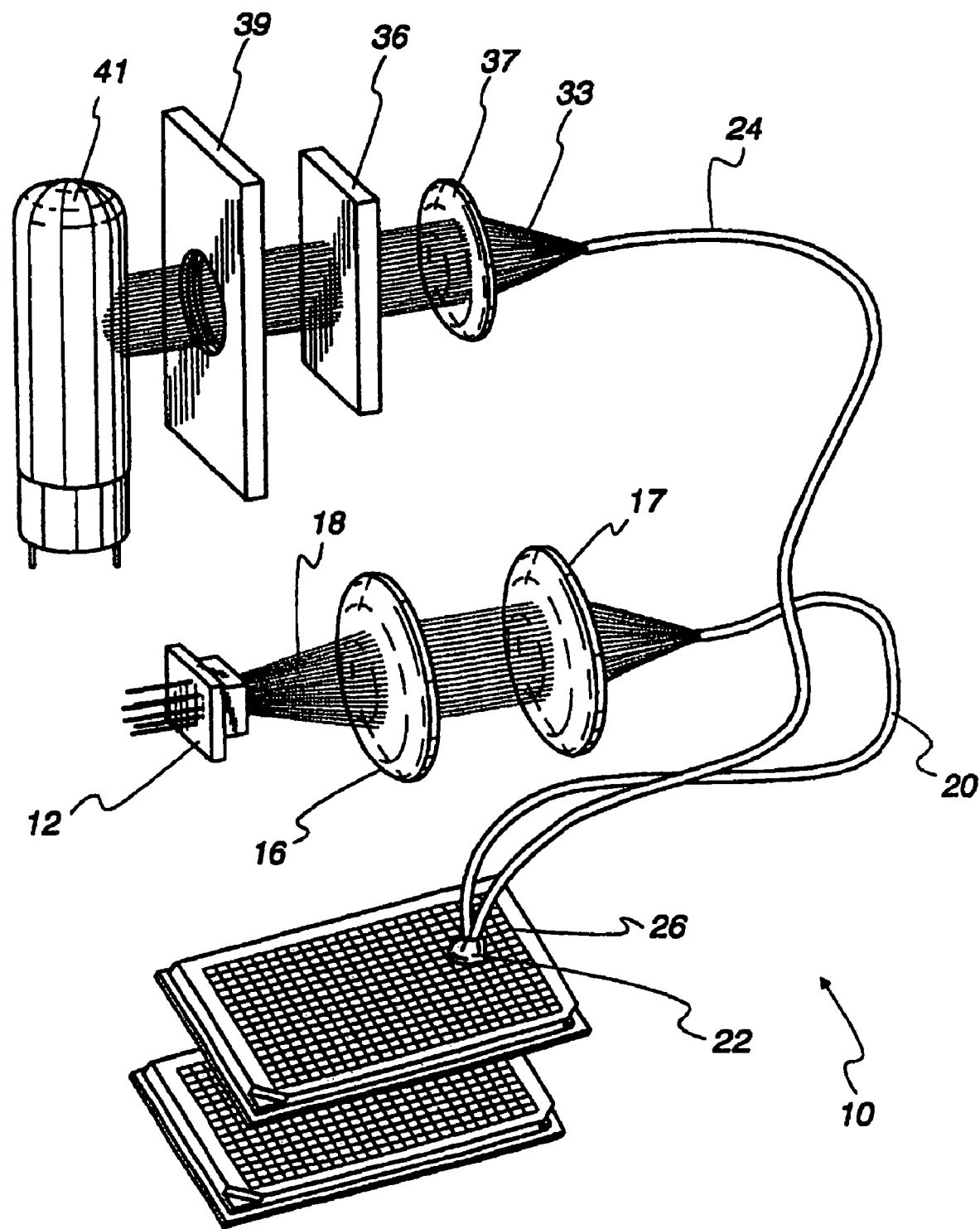
FIG. 1 is a schematic block diagram of a prior art optical unit of a measurement instrument.

FIG. 1 was already explained in the description of the prior art. In the following, the principle of the invention is first described referring to FIGS. 2A and 2B 2.

Figure 3:
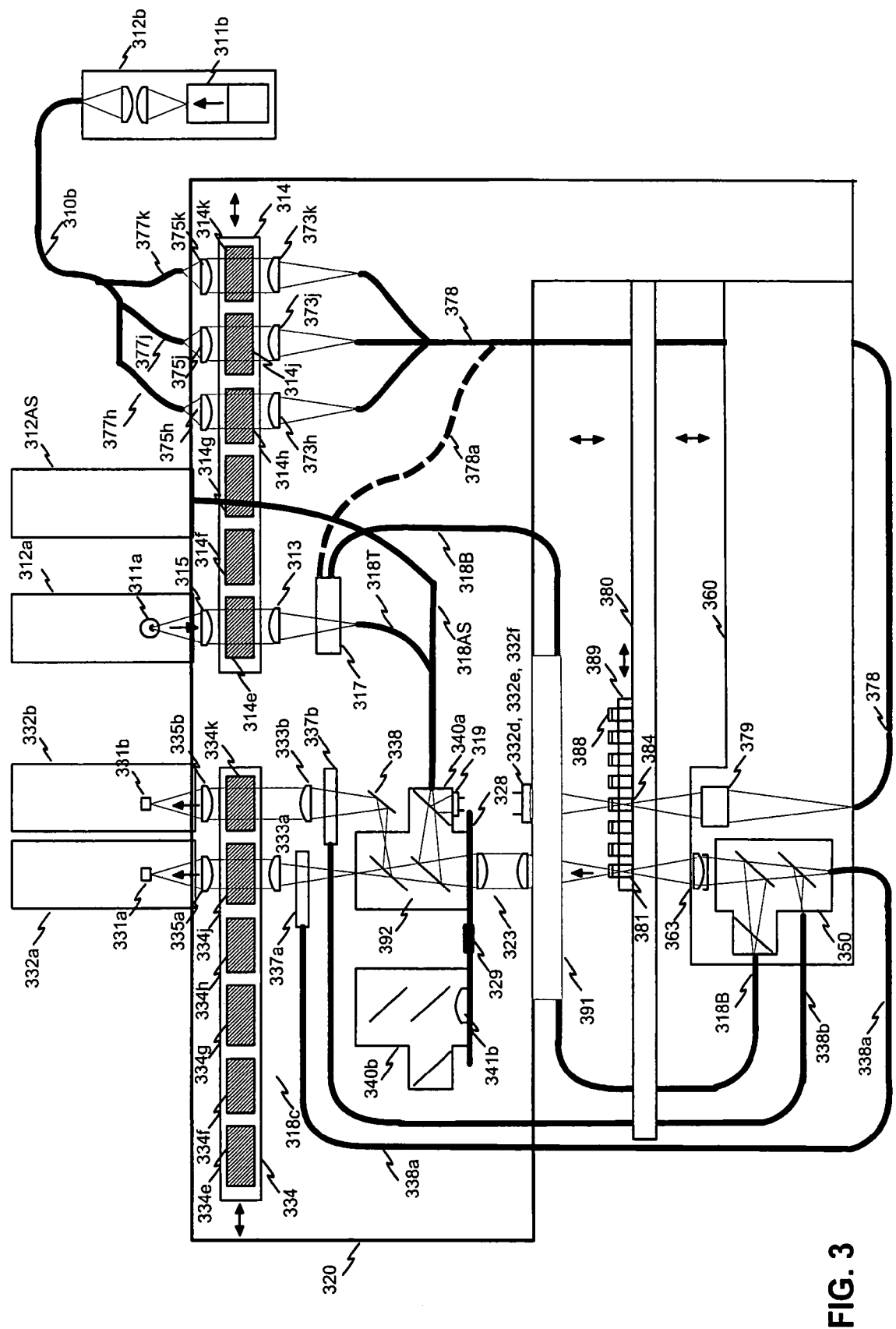
FIG. 3 is a schematic block diagram including a side view of an exemplary measurement instrument according to the invention.
Figure 4:
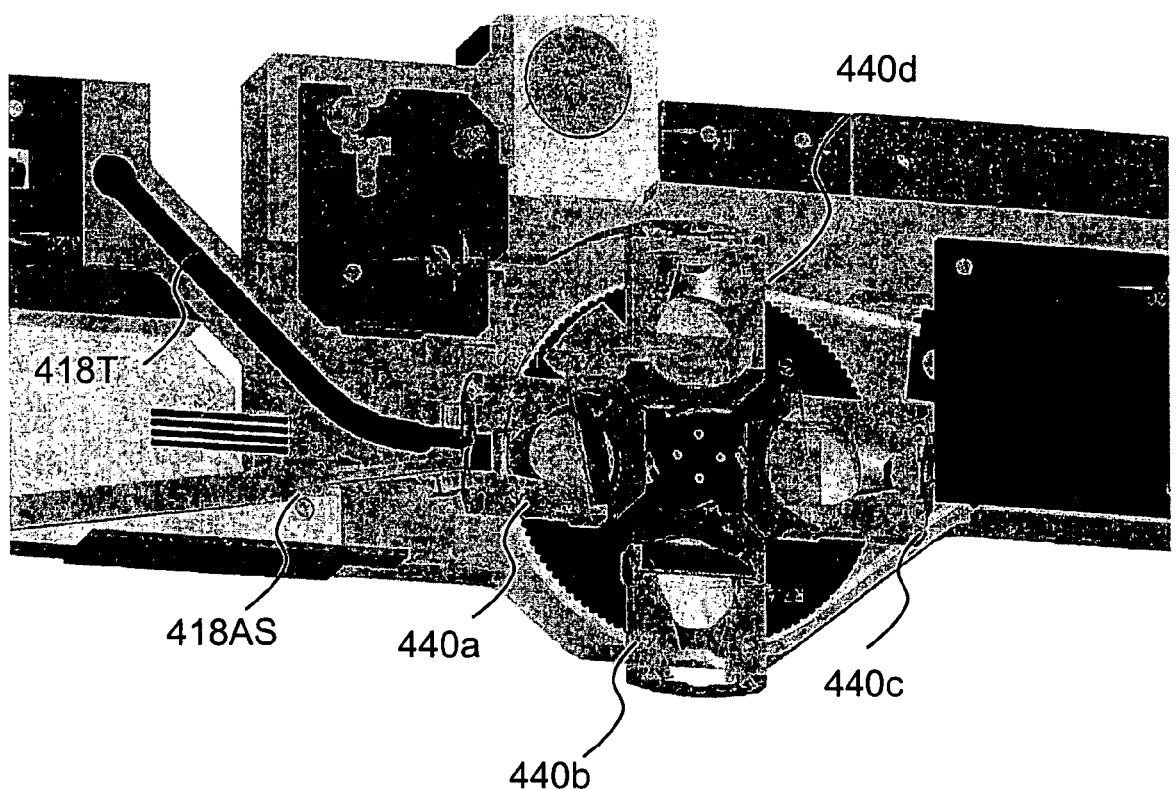
FIG. 4 is a top view of the optical module set and interface of an exemplary measurement instrument according to the invention.

Then, an example of a more detailed implementation is described referring to FIGS. 3 and 4, which illustrate exemplary analyser equipment according to the invention.

Figure 2A:
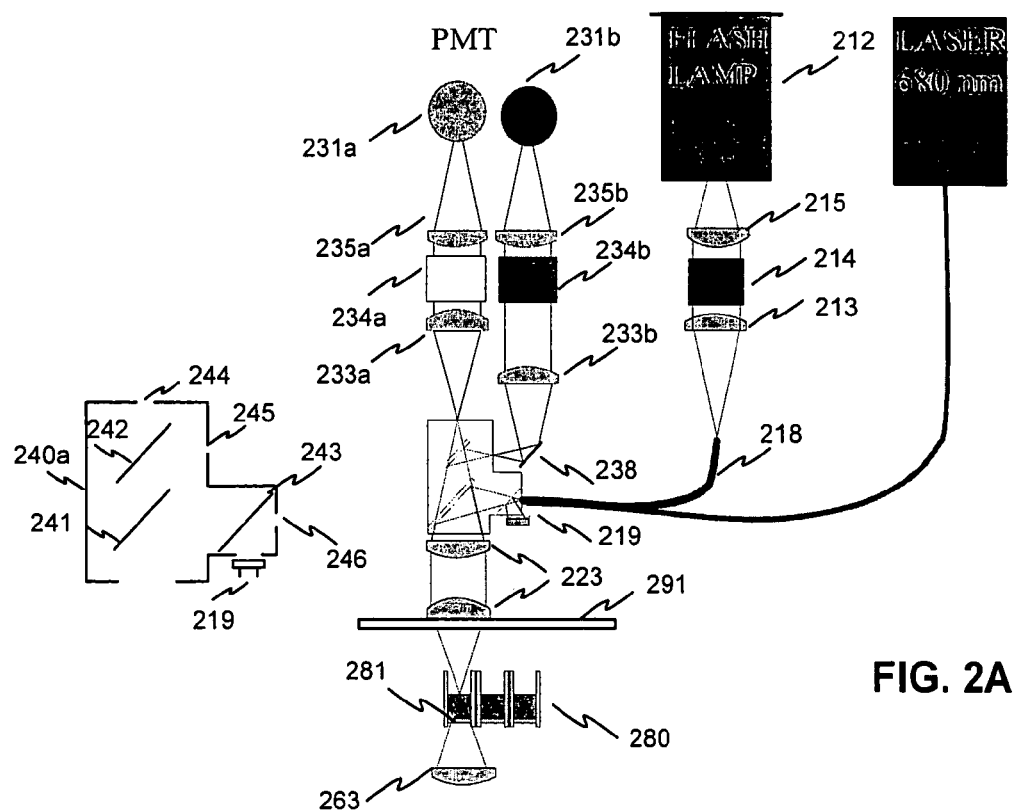
FIG. 2A is a schematic illustration of optical paths and main components of an exemplary optical unit for a measurement instrument according to the invention when used for photoluminescence measurement.
Figure 2B:
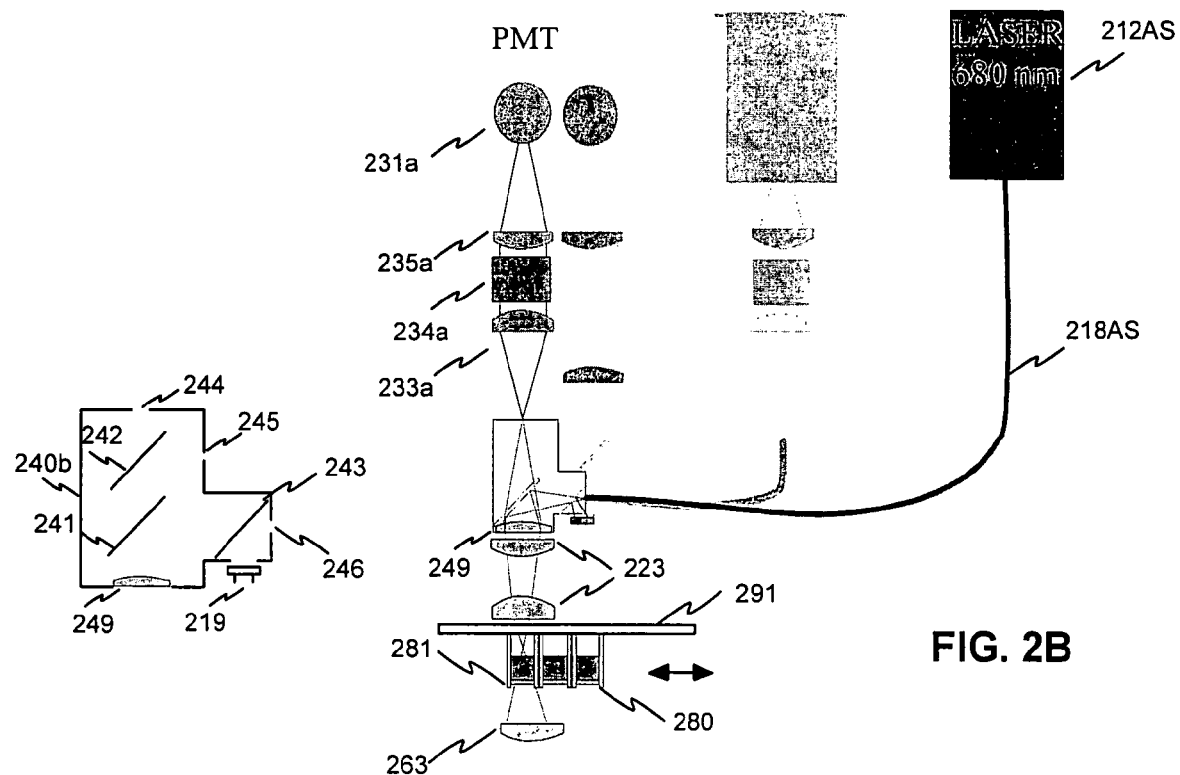
FIG. 2B is a schematic illustration of optical paths and main components of an exemplary optical unit for a measurement instrument according to the invention when used for AlphaScreen measurement.

FIGS. 2A and 2B illustrate main components and optical paths of an exemplary optical analyser instrument according to the invention. FIG. 2A shows a measurement mode for a photoluminescence measurement and FIG. 2B shows a measurement mode for an AlphaScreen measurement. The instrument comprises an illumination source 212 for the excitation of a sample in a photoluminescence measurement. The radiation from the lamp 212 is collimated with lens 215 and directed through an interference filter 214. Different filters can be selected for different wavelengths. The excitation beam is then focused to an end of a fibre optic guide 218, which guides it to an aperture 246 of an optical module (see the enlarged figure of the optical module). The fibre optic guide is preferably a bundle of fibres, such as 200 pieces of fibres with a diameter of 100 µm. One important purpose of the fibre optic guide is to mix the light of the illumination source in order to avoid an uneven distribution of excitation beam within the sample volume to be measured.

The excitation beam is guided through an aperture 246 of the optical module and reflected by a dichroic mirror 241 inside the optical module 240. The excitation beam is further directed into the sample 281 through an aperture of the optical module and a lens system 223. A part of the illumination light is reflected by a beam splitter mirror 243 and guided through an aperture into a reference detector in order to give reference information on the actual illumination intensity. While the reference mirror is located in the changeable mirror block, the excitation filter differences can be compensated by modifying the properties of the reference mirror. This way high feedback accuracy is achieved. A beam splitter mirror can be produced e.g. by forming reflective coating for the mirror to be e.g. stripes or dots, which cover only a part of the mirror surface.

The photoluminescence emission beam from-the sample 281 is directed with the lens system 223 through an aperture into the optical module 240, where it passes the (preferably) dichroic mirror 241. The dichroic mirror is preferably designed for each label so that it reflects excitation wavelength but transmits emission wavelengths. The emission beam is then divided inside the optical cube into to two beams by a second mirror 242. The mirror is preferably a dichroic mirror, which functions as a filter so that a beam with a wavelength of the first emission is transmitted through the mirror and focused through an aperture 244 according to the invention to the first detector 231a. The beam with a wavelength of the second emission is reflected and guided focused through another aperture 245 to the second detector 231b. The second dichroic mirror is therefore also preferably designed for each label/pair of labels so that it transmits first emission wavelengths but reflects second emission wavelengths.

The first emission beam received from the aperture of the optical module is collimated with a lens 233a and directed through an interference filter 234a in order to prevent light with a wavelength outside the first emission from passing to the first detector. The first emission beam is then focused with lens 235a to the first detector 231a. The second emission beam received from another aperture of the optical module is reflected with a mirror 238 to a lens 233b where the beam is collimated and directed through a second interference filter 234b in order to prevent light with a wavelength outside the second emission from passing to the second detector. The second emission beam is then focused with lens 235a to the first detector 231a. The signals received from the detectors are then amplified and processed to achieve a value for the intensities of the first and second emissions. The instrument may also comprise a bottom measurement head for measuring radiation below the sample, 263.

In the AlphaScreen measurement of FIG. 2B the excitation light is received from the laser source 212AS, and the beam is guided via an optical guide 218AS to the optical module. The light beam penetrates into the optical module preferably through an aperture and is further reflected towards the sample 281. The optical module comprises an additional lens 249 in order to adapt the focus to the shorter distance between the optical module and the sample. The distance is shortened by moving the measurement head or the assay in order to get the thermo plate 291 tightly sealed between the assay and the measurement head. In the AlphaScreen measurement only one detector 231a is used, preferably a photomultiplier tube.

According to the present invention, the alternative excitation light beams are guided into the optical module in slightly different angles.

FIG. 3 illustrates in more detail an exemplary optical instrument according to the invention. The instrument has a top measurement head 320, which includes components for providing an excitation beam and for detecting emissions from above the sample. The instrument has also an optional bottom measurement head 360, which includes components for providing an excitation beam and for detecting emissions from below the sample. The instrument further comprises a sample platform 380, which has means for moving and a sample tray 389 in order to position successive samples 381 into the measurement volume. There may also be means provided for adjusting the vertical position of the sample platform relative to the top and bottom measurement heads.

The instrument comprises a laser source 312AS for AlphaScreen measurements. The light of the laser is guided in an optical guide 318AS directly to the optical module 340a (340b). According to the present invention the light beam of the laser is directed to the optical module in a slightly different angle compared to the direction of the light beam of the photoluminescense measurements. The instrument also comprises a thermo plate 391 for keeping the temperature of the samples constant during the AlphaScreen measurements. In alphaScreen measurements the upper measurement head 320 or the sample platform 380 is shifted in order to have the thermo plate tightly between the assay and the upper measurement head. In FIG. 3 the optical module 340a is used for photoluminescence measurements; the module does not comprise a lens in the interface towards the sample. The optical module 340b is used for AlphaScreen measurements (when turned into the measurement position), and the module comprises a lens 341b in order to adjust the focus for a shorter distance. In this embodiment the detector 322a that is used for the AlphaScreen measurement is a photo-multiplier tube.

The optical modules may preferably be equipped with machine readable codes, such as bar codes, so that the processor of the equipment can check with a code reader, which type of optical modules are installed. The instrument is also preferably programmed to turn the correct type optical module to the measurement position. This way it can be certified that a correct type of optical module is used for each measurement. The bar code reader or related electronics are not shown in FIG. 3.

The instrument has another illumination source 312a for providing excitation in photoluminescence measurements. The illumination source 312a includes a pulse lamp, and the optical energy of each pulse is preferably equal. The excitation beam generated by the pulse lamp is collimated with a lens 315 and directed through an interference filter 314. The filter is placed on a filter slide, so that the excitation filter to be used in a measurement can be selected from several filters. The excitation beam is then focused to an end of a fibre optic guide 318, which mixes the excitation beam and guides it to an aperture of an optical module 340a, which is located behind the photo-multiplier tube. The optical module 340 and the lens system 323 directs the excitation beam into the sample 381. The optical module is not described here in more detail because it was explained in relation to FIG. 2.

The equipment may also include a further pulse lamp 312b, 311b, which may be a low power lamp, e.g. for simultaneous photometric measurements. The instrument has an optical fibre guide 312a for guiding the light from the second lamp. The light can be distributed for the photometric measurement into three filters 314h, 314j and 314k with fibre branches 377h, 377j and 377k.

The light beams are collimated with lenses 375h, 375j and 375k before directing the beams through the filters. The filters can be located on the same or different filter slide as the filter 314e for the first illumination source. If the same filter slide is used for filters of both lamps, the simultaneous measurement modes must be taken into account when the location of the filters is planned. After filtering, the beams are collimated into ends of three optical fibre cables 378, which are led to the bottom measurement head for the photometric measurement. The light beams from the optical cables 378 are focused to three samples 384 with a lens system 379 including lenses for each three beams. After transmitting through the samples the beams are measured with three detectors 322d, 322e and 322f, which are e.g. a photo diodes. The three ends of the fibre optic cables, three lenses, three simultaneously measured samples and three detectors are in this case located in a row perpendicular to the plane of the drawing and thus only one of them can be seen in the drawing.

It is preferable to have a separate optics for the photometrics measurement so that a photoluminescence measurement and a photometrics measurement/AlphaScreen measurement can be performed simultaneously from different samples. If simultaneous measurements are required, the analyzer is preferably equipped with separate pulse lamps. However, it is also possible to use an instrument with one pulse lamp for photometrics measurements. For example, an optical switch 317 may have an output for an optical fibre 378a, which leads light from the lamp 312a to the photometrics measurement optics 379. It is then possible to control the optical switch either to guide the light for providing excitation for an emission measurement or to guide the light the a photometric measurement.

An optical fibre 318T is used for guiding the excitation beam from the optical switch 317 to the optical module 340 of the top measurement head. An optical fibre 318B is used for guiding the excitation beam from the optical switch 317 to the optical module 350 of the bottom measurement head. The instrument may also have a further lamp so that different lamps can be selected for providing the excitation beam of the top head and the bottom head. In this case, a more versatile optical switch system is required.

The emission beam from the sample 381 is directed with the lens system 323 into the optical module 340 where the emission beam is divided into to two beams. A dichroic mirror in the optical module preferably functions as a filter so that a beam with a wavelength of the first emission is transmitted through the to the first detector 331a, and a beam with a wavelength of the second emission is reflected to the second detector 331b. The detector can be e.g. a photo-multiplier tube, which may be used in analogue mode or in photon count mode, or in both modes simultaneously. When the equipment includes detectors they may be of different types and the detection modes may be different during a photoluminescence measurement.

The first emission beam is collimated with a lens 333a and directed through an interference filter 334j in order to prevent light with a wavelength outside the first emission from passing to the first detector. The first emission beam is then focused with lens 335a to the first detector 331a. The second emission beam is reflected with a mirror 338 to a lens 333b where the beam is collimated and directed through a second interference filter 334k in order to prevent light with a wavelength outside the second emission from passing to the second detector. The second emission beam is then focused with lens 335a to the first detector 331a. The filters 334j and 334k are located on same filter slide or they may locate on different filter slides. The filter slide(s) is movable so that the filters used in the measurement can be selected from a number of filters with different pass-band wavelengths.

In an instrument also comprising a bottom measurement head there are optical switches 337a and 337b for selecting the detected emission beam from the top or bottom measurement head. An optical fibre 338a is used for guiding the first emission beam from the optical module 350 of the bottom measurement head 360 to the optical switch 337a. Another optical fibre 338b is used for guiding the second emission beam from the optical module 350 of the bottom measurement head 360 to the optical switch 337b.

The signals received from the detectors are then amplified and processed to achieve a value for the intensities of the first and second emissions. Measurement signals and reference signals are amplified and read after each excitation pulse and signal corrections are calculated. Basic references are determined with standard solvents after the analyzer has been assembled. If there are more than one excitation pulses used for one well, the corresponding emission signals are digitally integrated.

The instrument comprises a carousel wheel 328 for the attachment of optical modules 340a, 340b, . . . The wheel can be rotated around its fixing point 329, and the optical module used in a measurement can thus be selected by controlling the position of the wheel. According to the present invention, the equipment has an optical interface for at least two alternative excitation beams for optical modules.

If the instrument is equipped with a bottom measurement head, there may be a similar optical module 350 used in the bottom measurement head as in the top measurement head. The excitation and emission beams are lead between the two measurement heads with optical fibres 338a, 338b and 318B. There is also a lens system 363 for focusing the beams to the sample and ends of the optical fibres. Since the optical module of the bottom measurement head needs not be so frequently changed, it may be manually changeable. Alternatively a processor-controlled carousel can also be used in the bottom measurement head.

The photo-multiplier tube and its electronics as well as the light sources are shown reduced in size compared to other components in FIG. 3. On the other hand, the optical modules are shown essentially enlarged in FIG. 3 in order to better illustrate the optical paths in the instruments. The actual size of the optical modules may be as small as 20 mm×20 mm×20 mm. The optical modules may also have machine-readable identification codes.

The instrument is also equipped with electronics for amplifying and processing the signals from the detectors, as well as electronics for driving the lamp(s). There is also control electronics provided for controlling the measurements, such as selecting filter(s), selecting the optical module(s), controlling optical switch(es), controlling the position of the sample tray 389 for selecting the sample to be measured, and controlling the positions of the measurement heads 320 and 360 relative to the sample platform 380. The main electronics is not shown in FIG. 3, as the required electronics can be designed by a skilled person in the art.

FIG. 4 illustrates a top view of a set of optical modules in a top measurement head. The optical module 440a is at the measurement location. The module set also includes modules 440b, 440c and 440d. The module 440a receives the excitation light from the light guide 418T through an aperture of the optical module for the purpose of photoluminescence measurement. For AlphaScreen measurements the excitation light is guided to the optical module via guide 418AS, also through an aperture of the optical module. FIG. 4 clearly shows how the two alternative excitation light beams are applied to the module in slightly different angles. Light beams reach the mirror of the optical module at the same point of the vertical axis, which leads to the sample to be measured. The optical modules of the module set are preferably changeable.

Next some typical measurements other than AlphaScreen are described in more detail. In this description the use of an optical instrument according to FIG. 3 is referred to.

Chemiluminescence Measurement

In a chemiluminescence measurement no excitation pulse is given. The analogue gates or a digital window for the measurement period is set. After a sample is chosen a first period for measuring illumination is triggered. The length of the measurement period is e.g. 1 ms. Detected signals are read, further measurement periods are triggered, and the corresponding signals are read. The measurement periods are repeated for e.g. 1000 times, which gives 1 second for the total measurement time. Finally the measured signals are summed to achieve the result of the total measurement.

FI and TRF Measurements

In a prompt photoluminescence, i.e. FI measurement, one excitation pulse is given for each sample to be measured. In a FI measurement an excitation filter and an emission filter are selected as was described above. A suitable optical module is also selected; the optical module may be a general-purpose module, or it may be a module that is especially designed for a determined label substance.

After a sample has been chosen for the measurement an excitation pulse is transmitted, and reference $R_1$ is read wherein $R_i$ is the amount of light that has been used in the excitation of the label. The illumination reference is received from a reference detector 319. Emission signals $S1_A$ and $S1_B$ are then read from the detectors. A correction factor for the signals is calculated on the basis of the illumination reference value. The long-term stability of the equipment is fixed to this amount of light when using a determined excitation filter and mirror block.

If several excitation pulses are used for one sample, the sequence is repeated and the results are summed or averaged. This leads to improved signal-to-noise ratio of the measurement.

A time resolved photoluminescence measurement, i.e. TRF measurement, is equal to the FI measurement except that several excitation pulses are formed for each sample and corresponding emissions are measured. The measurement signals and reference signals are read after each excitation pulse and signal corrections are calculated. Basic references are determined with standard solvents after the analyzer has been assembled. After receiving all emission signals from a sample, the results are preferably digitally integrated. Finally, a linear correction can be made for the digital signal using a reference.

In this patent specification the structure of the components in an optical measurement instrument is not described in more detail as they can-be implemented using the description above and the general knowledge of a person skilled in the art.

An optical instrument includes control means for performing the optical measurement process. The control of the measuring process in an optical measurement instrument generally takes place in an arrangement of processing capacity in the form of microprocessor(s) and memory in the form of memory circuits. Such arrangements are known as such from the technology of analyzers and relating equipment. To convert a known optical instrument into an equipment according to the invention it may be necessary, in addition to the hardware modifications, to store into the memory means a set of machine-readable instructions that instruct the microprocessor(s) to perform the operations described above. Composing and storing into memory of such instructions involves known technology which, when combined with the teachings of this patent application, is within the capabilities of a person skilled in the art.

Above, an embodiment of the solution according to the invention has been described. The principle according to the invention can naturally be modified within the frame of the scope defined by the claims, for example, by modification of the details of the implementation and ranges of use.

The embodiments described above mainly relate to photoluminescence multiemission measurements and AlphaScreen measurements. However, even if the invention has special advantages when applied to such measurements, the invention can as well be applied in other types of measurements, such as single emission photoluminescence measurements and chemiluminescence measurements.

Although the invention has been described with reference to the different microtitration plates it is equally applicable to any form of sample matrix like gels and filter.

Although the invention is described with the arrangement where light sources and detectors are located on the top measurement head, there is no reason why their location on the bottom measurement head should not work.

In the embodiments described above the excitation light beams are directed to the optical module in the same horizontal plane. However, it is also possible to direct the beams in the same vertical or other plane and including an angle between the beams. However, the angle of the mirror in the optical module must be correspondingly adjusted.

The invention claimed is:

1. An optical measurement instrument for measuring a sample, comprising:
   a first illumination source for excitation of the sample in a first measurement mode;
   a detector for measuring emission from the sample;
   a second illumination source for excitation of the sample in a second measurement mode;
   a selectable optical module adapted to guide an excitation light beam to the sample; and
   directing means for directing a first excitation light beam from said first illumination source and a second excitation light beam from the second illumination source to said selectable optical module, said directing means being adapted to direct the first excitation light beam in a different angle to said selectable optical module than the second excitation light beam.

2. The instrument according to claim 1, wherein the first measurement mode is for measuring photoluminescence.

3. The instrument according to claim 1, wherein the second measurement mode is for measureng Amplified Luminescent Proximity Homogeneous Assay.

4. The instrument according to claim 1, wherein said selectable optical module is selectable between a first optical module and a second optical module, said first optical module comprising a first mirror for reflecting the first excitation light beam to the sample and said second optical module comprises a second mirror for reflecting the second excitation light beam to the sample, wherein the first mirror is in a different angle in the first optical module than the second mirror in the second optical module.

5. An optical measurement instrument for measuring a sample comprising:
   a first illumination source for excitation of the sample in a first measurement mode;
   a detector for measuring emission from the sample;
   a second illumination source for excitation of the sample in a second measurement mode; and
   a selectable optical module for guiding an excitation beam to the sample, said selectable optical module being selectable between a first optical module and a second optical module, wherein the second optical module and/or the first optical module comprises means for adjusting a focus between the second optical module and the sample for a shorter distance than a focus between the first optical module and the sample.

6. The instrument according to claim 5, wherein said means for adjusting is an additional lens towards the sample in the second optical module.

7. An instrument according to claim 5, further comprising a measurement head that includes said selectable optical module, an assay including said sample, and a thermo plate with a regulated temperature, wherein in said second measurement mode the thermo plate is placed closely between the measurement head and the sample assay.

8. The instrument according to claim 5, wherein the first measurement mode is for measuring photoluminescence.

9. The instrument according to claim 5, wherein the second measurement mode is for measuring Amplified Luminescent Proximity Homogeneous Assay.

* * * * *